United States Patent [19]

Frankhouser et al.

[11] 4,289,244

[45] Sep. 15, 1981

[54] SUPPORTING APPARATUS FOR MEDICAL BOTTLES AND THE LIKE

[75] Inventors: Douglas L. Frankhouser, Fountain Valley; Louis Schnitz; Joseph C. Greenstadt, both of Los Angeles, all of Calif.

[73] Assignee: The Lightron Corporation, Huntington, N.Y.

[21] Appl. No.: 967,687

[22] Filed: Dec. 8, 1978

[51] Int. Cl.³ ............................................. A61B 19/00
[52] U.S. Cl. ..................................... 211/117; 248/318; 248/297.3; 248/297.5
[58] Field of Search ............ 248/295 B, 295 C, 311.3, 248/318, 327, 333, 336, 337, 408, 409, 412; 211/117

[56] References Cited

U.S. PATENT DOCUMENTS

| | | | |
|---|---|---|---|
| 812,396 | 2/1906 | Bewyer | 248/336 |
| 842,717 | 1/1907 | Smith | 248/336 |
| 1,103,839 | 7/1914 | Rellay | 248/412 |
| 1,859,223 | 5/1932 | Stevenson | 248/412 |
| 2,664,259 | 12/1953 | Rose | 248/337 |
| 3,006,481 | 10/1961 | Gussack | 211/117 |
| 3,191,904 | 6/1965 | Karapita | 248/333 |
| 3,321,090 | 5/1967 | Greenstadt | 211/162 |
| 3,642,241 | 2/1972 | Kaufman | 248/327 |
| 3,770,236 | 11/1973 | Marsh et al. | 248/408 |
| 4,005,844 | 2/1977 | Richmond | 248/311.3 |
| 4,047,687 | 9/1977 | Turner | 248/318 |

FOREIGN PATENT DOCUMENTS 27493 of 1907 United Kingdom ............ 248/295 C

Primary Examiner—William H. Schultz
Attorney, Agent, or Firm—Subkow and Kriegel

[57] ABSTRACT

Apparatus for supporting intravenous bottles, or the like, which includes a first elongate rod member adapted to be suspended from the ceiling, and a second elongate rod member telescopically related to the first member, and depending therefrom. A bottle supporting structure is adjustable lengthwise along the second member and is secured at different locations along the second member by a readily accessible first lock device disposed substantially below a second lock device that releasably secures the second member to the first member at different locations therealong, the second lock device being controlled by a mechanism operated from a remote location along the second member positioned below the bottle supporting structure. By virtue of the above apparatus, the rod members can be adjusted with respect to each other to enable the same apparatus to be used in rooms having different ceiling heights, the bottle supporting structure being shiftable to convenient desired locations along the second rod member.

10 Claims, 8 Drawing Figures

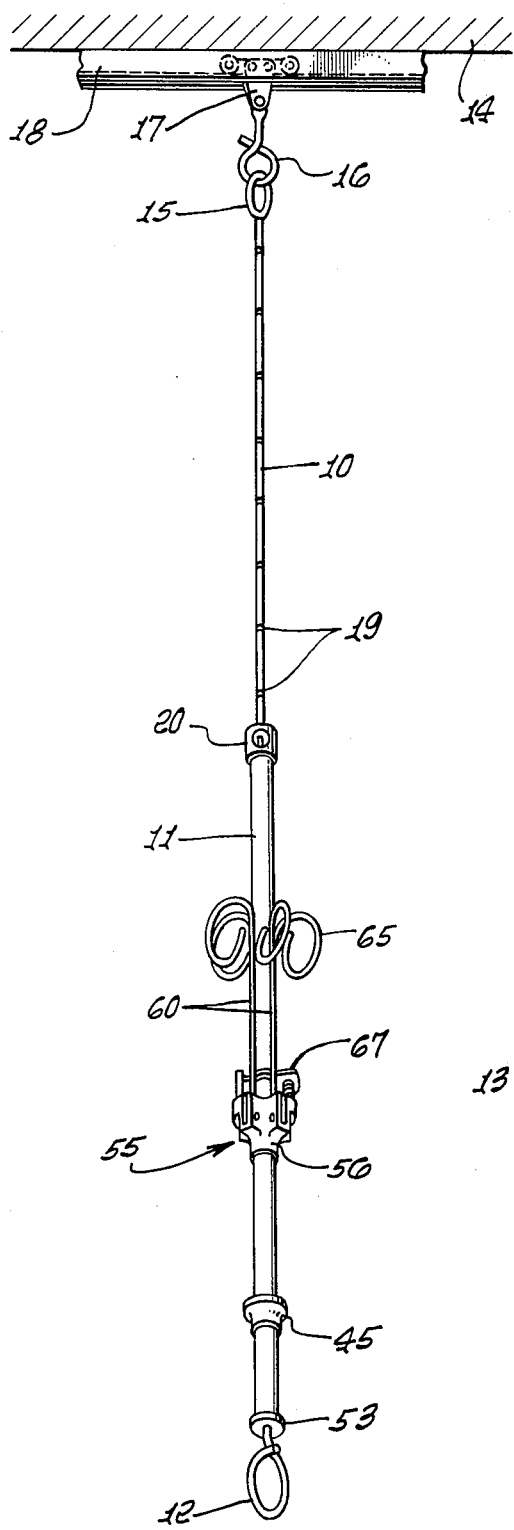
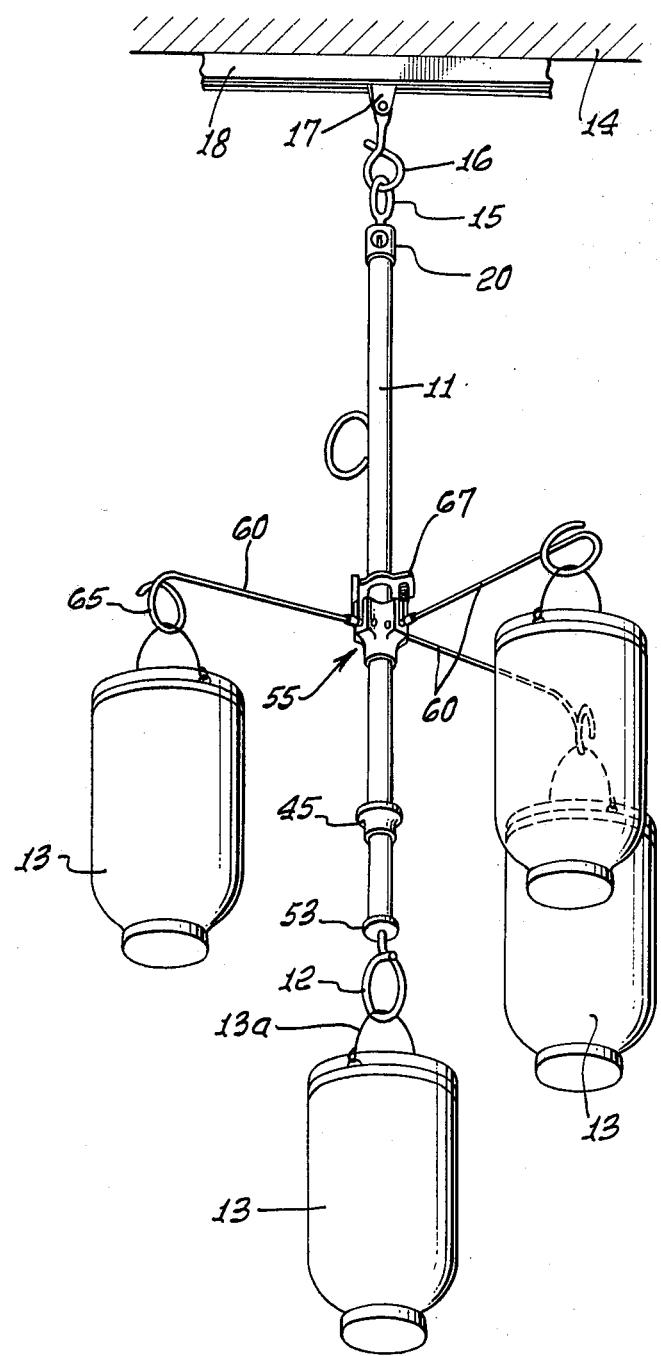

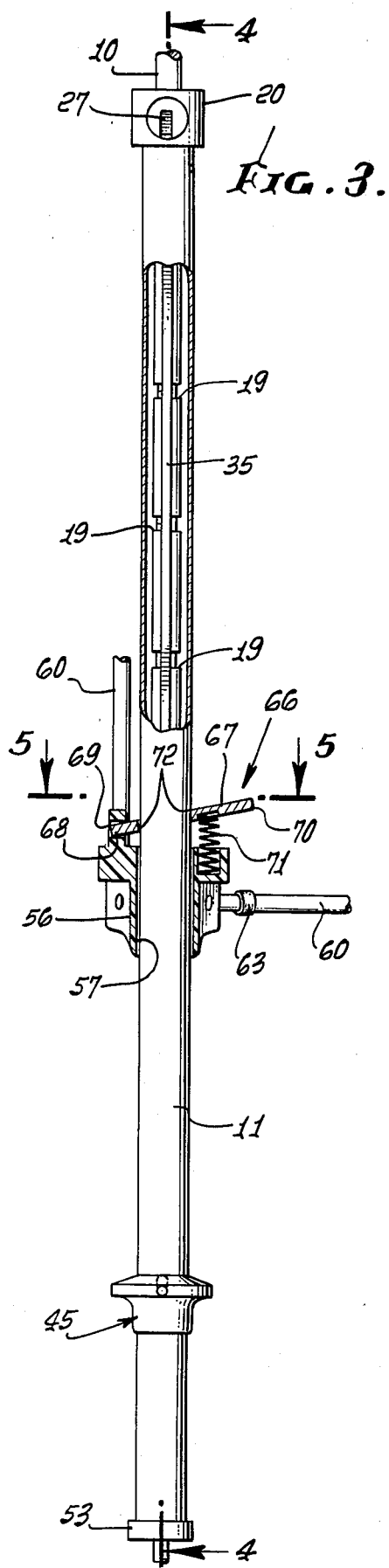
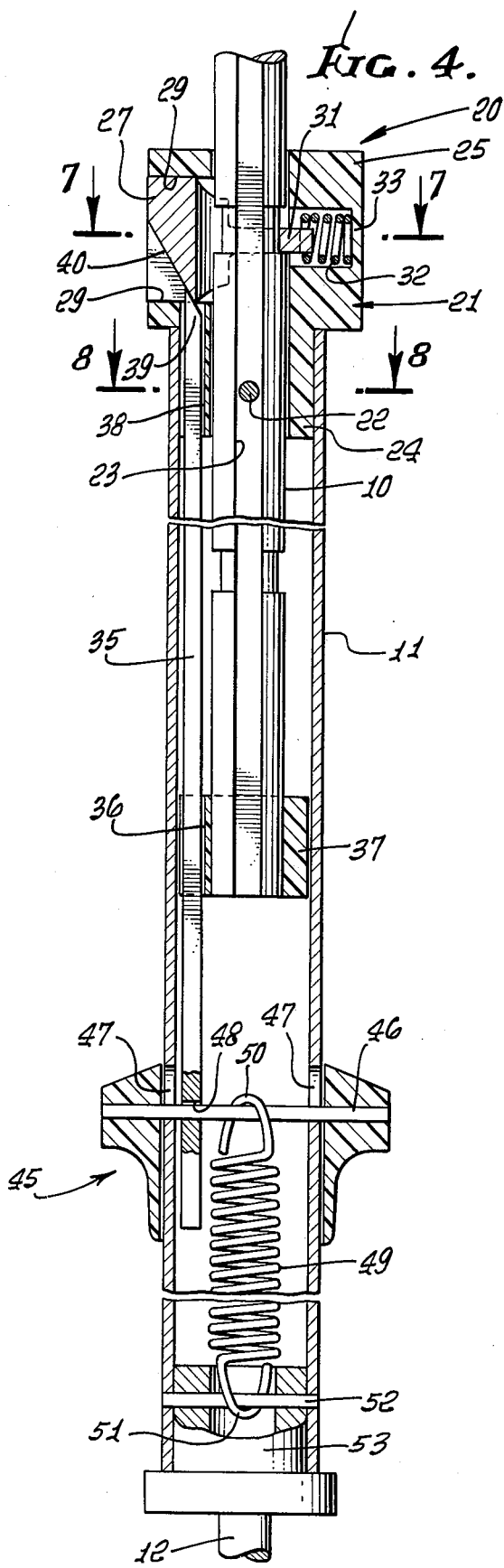

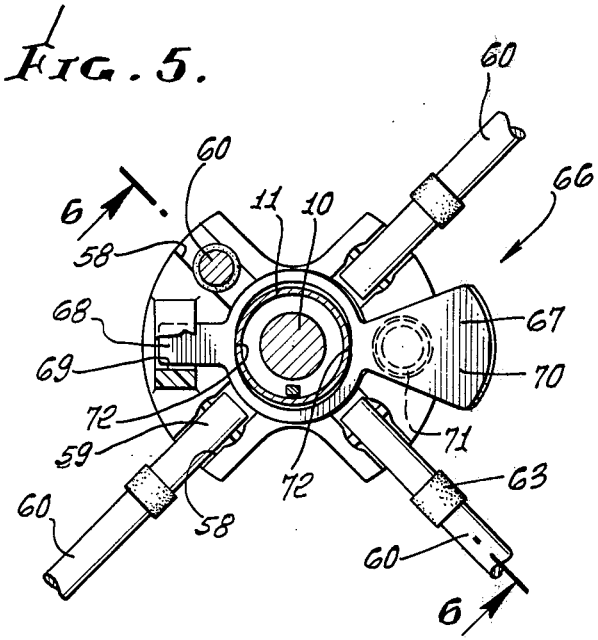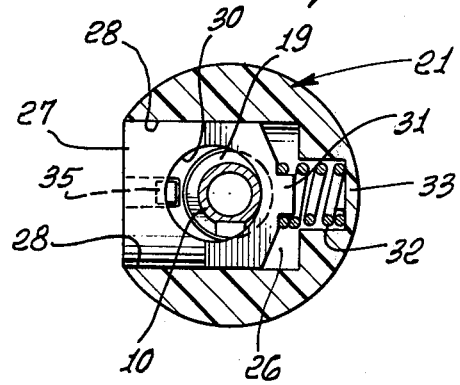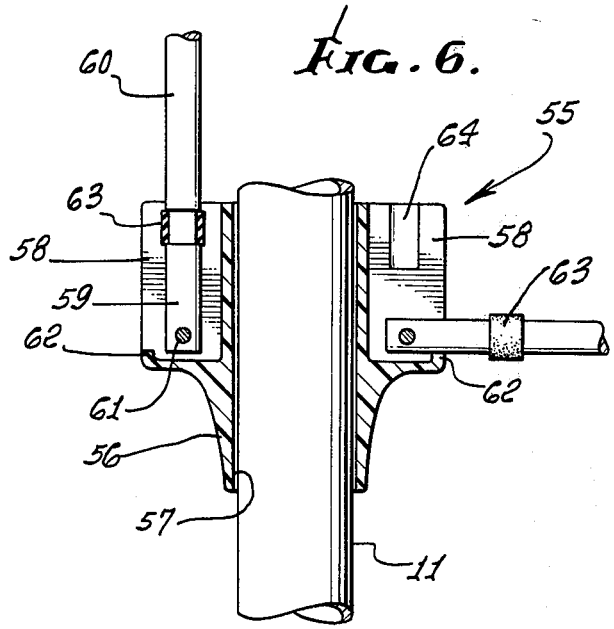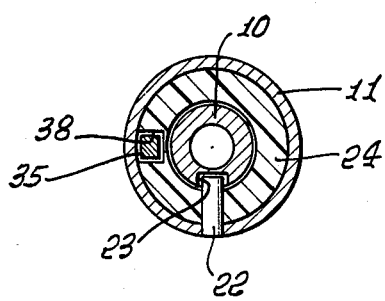

SUPPORTING APPARATUS FOR MEDICAL BOTTLES AND THE LIKE

The present invention relates to apparatus for supporting bottles, and the like, used in intravenous feedings.

In U.S. Pat. No. 3,321,090, a supporting apparatus is illustrated in which a bottle supporting structure is secured at selected locations along the length of a rod member than can be supported from a ceiling. Since ceiling heights vary, it becomes necessary to provide rod members of different lengths to enable the bottles to be supported at an appropriate height with respect to the patient receiving the intravenous feeding. The production of different size rod members increases manufacturing and inventory costs.

In U.S. Pat. No. 3,006,481, an adjustable rod structure is disclosed consisting of two rod members telescopically related to each other. A lock device is mounted on the upper member and is received in a selected groove in a lower member for the purpose of adjusting the distance of the bottle supporting structure below the ceiling from which the apparatus is supported. The lock device may be inconvenient to operate by nurses of short height standing on the floor of the room. Additionly, the bottle supporting structure is fixed in position with respect to the lower rod member, and cannot always be placed at the most optimum position for the patient receiving the intravenous feeding.

In U.S. Pat. No. 3,191,904, a supporting unit is illustrated and described which has telescopic members that are adjustable with respect to one another to change the effective length of the unit, which are locked to one another by a control device at the lower end of the unit. However, there are no provisions made for adjusting the location of the bottle supporting structure with respect to the telescopic rod mechanism itself.

In the apparatus illustrated in the drawings, the need for providing a plurality of different size supporting rod members for use with different height ceilings is eliminated. Not only can the effective length of the rod members be varied, but the location of the bottle supporting structure with respect to the rod members can also be adjusted. The adjustments can be made readily from the floor of the room in which the apparatus is to be mounted by persons of short stature, since the mechanisms for telescopically adjusting the rod members with respect to one another, and the bottle supporting structure with respect to the rod members, are readily accessible to both tall and short persons standing on the floor of the room. The location of the bottle supporting structure can be so selected as to achieve the greatest amount of gravitational feed to the patient of the intravenous fluids.

An object of the present invention is to provide an apparatus in which elongate telescopic rod members can be adjusted in overall length with respect to each other and secured together by a lock mechanism which is disposed a substantial distance above the location from which the lock mechanism is operated, thereby rendering operation of the lock device easy to perfrom by short persons as well as tall persons.

A further object of the invention is to provide an apparatus for supporting medical bottles, and the like, which includes telescopically related members that are secured in a desired telescoped position by an upper lock mechanism operated from a remote point well below the point at which the bottle supporting structure is mounted on the telescopic mechanism, the bottle supporting structure being releasably secured in various positions by a lower lock mechanism positioned at a convenient point above the room floor and readily accessible to persons of small stature. In a more limited sense, the lock mechanism for securing the bottle supporting structure to the telescopic members can be adjusted by infinitesimal amounts along the length of the telescopic members to insure placement of the intravenous bottles at the desired position.

Another object of the invention is to provide an apparatus for supporting intravenous bottles, and the like, in which telescopically related members can be adjusted in overall length and positively locked to one another at a plurality of positions, a bottle supporting structure also being adjustably mounted with respect to the telescopic members and secured in its desired position of adjustment, both lock mechanisms being easily operable by short or tall persons standing on the floor of the room. The locking effect of the lock mechanism for the bottle supporting structure is automatically increased upon increase in the gravitational effect of the bottle supporting structure, bottles and their contents.

This invention possesses many other advantages, and has other purposes which may be made more clearly apparent from a consideration of a form in which it may be embodied. This form is shown in the drawings accompanying and forming part of the present specification. It will now be described in detail, for the purpose of illustrating the general principles of the invention; but it is to be understood that such detailed description is not to be taken in a limiting sense.

Referring to the drawings:

FIG. 1 is a side elevational view of an apparatus embodying the invention, with the parts in a relatively extended position, and with bottle supporting arms in a retracted position;

FIG. 2 is an enlarged view similar to FIG. 1 disclosing the rod portion of the apparatus in a fully collapsed position with the bottles suspended from the supporting arms;

FIG. 3 is an enlarged side elevational view, with parts disclosed in longitudinal section, of a portion of the apparatus disclosed in a fully telescoped position;

FIG. 4 is a further enlarged longitudinal sectional view disclosing the upper lock portion of the apparatus and its remotely controlled lock actuator;

FIG. 5 is an enlarged cross-section taken along the line 5—5 on FIG. 3;

FIG. 6 is a section taken along the line 6—6 on FIG. 5;

FIG. 7 is a cross-section taken along the line 7—7 on FIG. 4; and

FIG. 8 is a cross-section taken along the line 8—8 on FIG. 4.

The apparatus disclosed in the drawings includes an elongate upper rod member 10 shiftable relatively longitudinally within an elongate lower tubular rod member 11, the lower end of which may be provided with a spiral safety hook 12 on which an intravenous bottle 13 can be hung, the bottle having a bail 13a supported by the lower hook. The upper rod member 10 may be secured directly to a ceiling 14, or it may be movably mounted with respect to the ceiling by having its upper eye 15 supported by a spiral safety hook 16 pivotally mounted on a carrier 17 shiftable along a track 18 suitably secured to the room ceiling.

The upper rod member 10 had a plurality of longitudinally spaced locking peripheral grooves 19, the rod member 10 passing into the tubular rod member 11 and through a lock device 20 fixed to the upper end of the outer tubular member (see FIG. 4). The lock device includes an upper lock body 21 through which the upper rod member 10 is slidable, rotation between the upper and lower rod members being prevented by a radial pin 22 secured to the outer tubular member and projecting into a longitudinal elongate groove 23 in the upper rod member 10. The lower portion 24 of the lock body is reduced in diameter and fits snugly into the upper end of the outer tubular member 11, being suitably secured thereto. The lock body is enlarged at its upper portion 25 and has a chamber 26 therein receiving a lock member 27 slidable laterally in the upper lock body along opposed side walls 28 of the lock body and also along the upper and lower walls 29 of the body.

The lock member has a vertical opening 30 therethrough through which the upper rod member 10 is movable when the lock is released, as described below, this lock member including a bolt portion 31 shiftable into a selected rod groove 19 by a compression spring 32 bearing against the lock member and against a spring seat 33 in the body. When in this position, the upper and lower rod members 10, 11 are locked to one another against relative longitudinal movement. When the lock member 27 is shifted inwardly against the force of the spring, the bolt 31 is removed from the groove, permitting the tubular member 11 to be shifted longitudinally in both directions.

As specifically disclosed, the lock member 27 is shifted to an unlocked position by an elongate release rod 35 located within the outer tubular member 11, passing through a groove 36 in a guide bushing 37 affixed to the lower end of the upper rod member 10, the release rod also passing through a guide groove 38 in the lower portion 24 of the upper lock body. The upper end 39 of the rod is tapered to provide a cam surface which engages a companion cam surface 40 on the lock member 27, so that upward movement of the release rod 35 within the outer tubular member causes the rod cam 39 to engage the lock cam 40 to shift the lock member towards the right, as seen in FIG. 4, against the force of the spring 32 to remove the bolt portion 31 of the lock from the peripheral groove 19, which then allows the outer tubular member 11 to be shifted upwardly or downwardly to the desired extent with respect to the elongate upper rod member 10.

The lock member 27 is actuated from a location near the lower end of the outer tubular member 11. As shown, a release or actuator knob 45 is slidably mounted on the outer tubular member and has a transverse pin 46 secured thereto, extending through diametrically opposed vertical slots 47 in the outer tubular member and through a hole or opening 48 in the release rod 35. Normally, the release knob 45 and the release rod are disposed in a lower position along the outer tubular member 11 by a tensile spring 49 which has an upper hook 50 engaging the transverse pin 46 and a lower hook 51 engaging a lower pin 52 fixed in a lower bushing 53 that closes the lower end of the outer tubular member. When the release rod 35 is elevated by the knob 45 in opposition to the force of the tensile spring 49, the rod is carried upwardly therewith to the extent determined by engagement of the transverse pin 46 with the upper ends of the slots 47, the actuating cam surface 39 engaging the lock member cam surface 40 and shifting the lock member 27 to rod releasing position. When the knob is released, the tensile spring 49 pulls it to its initial or downward position, retracting the release rod 35 and permitting the helical compression spring 32 to shift the lock member to the left, seen in FIG. 4, positioning the bolt 31 within a selected rod groove 19 to secure the upper and lower rod members 10, 11 against relative movement.

A bottle supporting structure 55 is slidable along the outer tubular member 11 and can be locked in any selected position along its exterior. It is to be noted that the body 56 of the supporting structure is disposed above the release knob 45, and that it has a central bore 57 through which the outer tubular member 11 passes. The body of the supporting structure has circumferentially spaced slots 58 therein, each of which receives the inner portion 59 of a bottle carrying arm 60 that is pivotally mounted on a pin 61 extending across the slot and suitably attached to the body on opposite sides thereof. Each arm 60 can extend outwardly to a substantially horizontal position, as determined by engagement of the inner portion 59 of each arm with a suitable body stop 62. Each arm can be swung upwardly to a position adjacent to the outer tubular member, as disclosed in FIG. 1, each arm being releasably retained in that position by an elastic retainer member 63 secured to the arm and which expands slightly into a vertical notch 64 in one of the side walls of the slot. The outer end of each arm is formed as a spiral safety support hook 65 from which the bail of the bottle 13 extends.

The body 56 of the bottle supporting structure can be releasably secured to the outer tubular member 11 at an infinite number of positions between the limit of upward travel of the body along the outer tubular member and the lower limit of travel adjacent to the upper end of the release knob 45. A one-way clutch type device 66 is provided (see FIG. 3), which includes a gripping member 67 through which the outer tubular member 11 extends, having one end 68 pivotally mounted within an opening 69 in the body, the opposite end of the gripping member being formed as a release tab 70 which is engaged by a helical compression spring 71 bearing against the underside of the tab, the lower end of the spring bearing against the structure body 56. The gripping member is urged to its inclined position disclosed in FIG. 3 which causes the opposite edges 72 of the gripping member to bear against the periphery of the outer tubular member 11, providing a friction lock between the gripping member 67 and the exterior of the tubular member. The weight of the bottles 13 and their contents causes the opposed edges 72 of the wafer-like lock 67 to dig into the periphery of the outer tubular member 11, insuring the retention of the supporting structure 55 in its locked position against the outer member.

When it is desired to shift the supporting structure to a different position along the outer member, the tab 70 is depressed against the force of the spring 71 to shift the lock member 67 from the outer member 11 and permitting the supporting structure 55 to be shifted to any other desirable location. Release of the unlocking force on the lock member 67 causes the compression spring 71 to reshift the tab to its inclined and tubular member gripping position.

The combination and positions of the two locking devices makes it possible for persons of short height, as well as tall persons, to readily and conveniently adjust the effective length of the telescopic rod structure and enable a single size apparatus to be used in connection with different height ceilings. Once the desired length of the telescopic rod member structure has been selected, the upper lock 20 is readily released to permit the lower tubular member 11 to be shifted with respect to the upper rod member 10, the two rod members then being secured to each other against longitudinal movement. Thereafter, the bottle supporting structure 55 can be shifted to the desired position by persons of different heights standing on the floor, it being a relatively simple operation to release the one-way gripping member 67, slide the bottle supporting structure to the desired location, and then release the one-way gripping member, which is automatically shifted by the spring 71 back to its gripping position.

With respect to the remote controlled upper lock device, it is only necessary for the release knob 45 to be actuated to release the lock 20 and permit the outer tubular member 11 to be elevated a short distance and position the bolt 31 out of the groove 19, whereupon the upper lock member will slide along the periphery of the upper rod, and, upon reaching the next groove 19 on the rod, the lock will automatically be shifted by the spring 32 into the next groove, positively locking the rods to one another, until the release rod 35 is again actuated to cam the lock member to its unlocked position. With respect to the lower lock device, it will instantly grip the periphery of the outer tubular member 11 and lock the bottle supporting structure thereto without any longitudinal movement first being required.

We claim:

1. A supporting apparatus for bottles and the like comprising an upper elongate rod member, a lower elongate tubular rod member receiving said upper member and movable longitudinally therealong, a first lock member mounted on the upper portion of said lower rod member and movable into locking engagement with said upper rod member to lock said members together and thereby adjust the overall effective length of said rod members, operating means engaging said first lock member for shifting said first lock member into locking engagement with said upper rod member, a body structure slidable along said lower member and adapted to support one or more bottles, a second lock member carried by said body structure and engaging said lower member to releasably secure said body structure to said lower member at different locations along said lower member, lock releasing means on said lower member for releasing said first lock member from said upper member including an actuator disposed on and slidable along the exterior of said lower member below said body structure, a release rod in said lower member connected to said actuator and having an upper portion thereon engageable with said first lock member to shift said first lock member from locking engagement with said upper rod member in response to upward movement of said actuator and release rod along said lower member, and means for moving said actuator and release rod downwardly along said lower member to enable said operating means to reshift said first lock member into locking engagement with said upper rod member.

2. Apparatus as defined in claim 1, said operating means comprising a spring bearing against said first lock member.

3. Apparatus as defined in claim 2, said spring being a helical compression spring.

4. A supporting apparatus for bottles and the like comprising an upper elongate rod member, a lower elongate tubular rod member receiving said upper member and movable longitudinally therealong, a first lock member mounted on the upper portion of said lower rod member and movable into locking engagement with said upper rod member to lock said members together and thereby adjust the overall effective length of said rod members, operating means engaging said first lock member for shifting said first lock member into locking engagement with said upper rod member, a body structure slidable along said lower member and adapted to support one or more bottles, a second lock member carried by said body structure and engaging said lower member to releasably secure said body structure to said lower member at different locations along said lower member, lock releasing means on said lower member for releasing said first lock member from said upper member including an actuator disposed on said lower member below said body structure, a release rod in said lower member connected to said actuator and having an upper portion thereon engageable with said first lock member to shift said first lock member from locking engagement with said upper rod member in response to upward movement of said actuator and release rod along said lower member, means for moving said actuator and release rod downwardly along said lower rod member to enable said operating means to reshift said first lock member into locking engagement with said upper rod member; said upper portion of said releasing rod comprising a tapered cam surface slidably engaging said first lock member.

5. Apparatus as defined in claim 4; said tapered cam surface slidably engaging a companion cam surface on said first lock member.

6. A supporting apparatus for bottles and the like comprising an upper elongate rod member, a lower elongate tubular rod member receiving said upper member and movable longitudinally therealong, a first lock member mounted on the upper portion of said lower rod member and movable into locking engagement with said upper rod member to lock said members together and thereby adjust the overall effective length of said rod members, operating means engaging said first lock member for shifting said first lock member into locking engagement with said upper rod member, a body structure slidable along said lower member and adapted to support one or more bottles, a second lock member carried by said body structure and engaging said lower member to releasably secure said body structure to said lower member at different locations along said lower member, lock releasing means on said lower member for releasing said first lock member from said upper member including an actuator disposed on said lower member below said body structure, a release rod in said lower member connected to said actuator and having an upper portion thereon engageable with said first lock member to shift said first lock member from locking engagement with said upper rod member in response to upward movement of said actuator and release rod along said lower member, means for moving said actuator and release rod downwardly along said lower rod member to enable said operating means to reshift said first lock member into locking engagement with said upper rod member; said means for moving said actuator and release rod downwardly comprising a spring operatively connected to said actuator and release rod.

7. Apparatus as defined in claim 6, said spring being a helical tension spring within said lower member connected to said actuator and release rod.

8. A supporting apparatus for bottles and the like corresponding an upper elongate rod member, a lower elongate tubular rod member receiving said upper member and movable longitudinally therealong, a first lock member mounted on the upper portion of said lower rod member and movable into locking engagement with said upper rod member to lock said members together and thereby adjust the overall effective length of said rod members, operating means engaging said first lock member for shifting said first lock member into locking engagement with said upper rod member, a body structure slidable along said lower member and adapted to support one or more bottles, a second lock member carried by said body structure and engaging said lower member to releasably secure said body structure to said lower member at different locations along said lower member, lock releasing means on said lower member for releasing said first lock member from said upper member including an actuator disposed on said lower member below said body structure, a release rod in said lower member connected to said actuator and having an upper portion thereon engageable with said first lock member to shift said first lock member from locking engagement with said upper rod member in response to upward movement of said actuator and release rod along said lower member, means for moving said actuator and release rod downwardly along said lower rod member to enable said operating means to reshift said first lock member into locking engagement with said upper rod member; said operating means comprising a spring bearing against said first lock member; said spring being a helical compression spring; said upper portion of said release rod comprising a tapered cam surface slidably engaging said first lock member.

9. Apparatus as defined in claim 8, said tapered cam surface slidably engaging a companion cam surface on said first lock member.

10. Apparatus as defined in claim 9; said means for moving said actuator and release rod downwardly comprising a spring operatively connected to said actuator and release rod, said spring being a helical tension spring within said lower member connected to said actuator and release rod.

* * * * *